(12) United States Patent
Da Cruz

(10) Patent No.: US 6,613,577 B1
(45) Date of Patent: Sep. 2, 2003

(54) USE OF BATHOCUPROINE FOR THE EVALUATION OF THE ANTIOXIDANT POWER IN LIQUIDS AND SOLUTIONS

(75) Inventor: Giuseppe Da Cruz, San Germano Vercellese (IT)

(73) Assignee: Med. Dia SRL., San Germano Vercelles (IT)

( * ) Notice: Subject to any disclaimer, the term of this patent is extended or adjusted under 35 U.S.C. 154(b) by 0 days.

(21) Appl. No.: 09/787,270

(22) PCT Filed: Sep. 15, 1999

(86) PCT No.: PCT/IT99/00289

§ 371 (c)(1),
(2), (4) Date: May 9, 2001

(87) PCT Pub. No.: WO00/16093

PCT Pub. Date: Mar. 23, 2000

(30) Foreign Application Priority Data

Sep. 16, 1998 (IT) .......................................... VC98A0012

(51) Int. Cl.$^7$ ............................................... G01N 21/62
(52) U.S. Cl. .............................. 436/171; 436/2; 436/12; 436/60; 436/73; 436/80; 436/166
(58) Field of Search ................................ 436/2, 12, 16, 436/60, 73, 80, 164, 165, 171, 172

(56) References Cited

U.S. PATENT DOCUMENTS 5,254,590 A    10/1993   Malen et al.

FOREIGN PATENT DOCUMENTS

EP    0 760 483    3/1997

OTHER PUBLICATIONS

Bagnati et al. "Cu(I) availability paradoxically antagonizes antioxidant consumption and lipid peroxidation during the initiation phase of copper–induced LDL oxidation", Biochemical and Biophysical Research Communications (1998), 253(2), 235–240.*

Bijloo et al. "Copper complexes of 1, 10–phenanthroline and related compounds as superoxide dismutase mimetics", Journal of Inorganic Biochemistry (1990), 40(3), 237–44.* www.oxfordbiomed.com/PDF–Kit%20Inserts/ta02.pdf: "Total Antioxidant Power", Oxford Biomedical Research, Mar. 2001.* by Rakesh P. Patel et al., "Reduction of Cu(II) by lipid hydroperoxides: implications for the copper–dependent oxidation of low–density lipoprotein", Biochemical Journal, vol. 322, No. 2, 1997, pp. 425–433.

* cited by examiner

Primary Examiner—Jill Warden
Assistant Examiner—Yelena Gakh
(74) Attorney, Agent, or Firm—Young & Thompson

(57) ABSTRACT

The antioxidant power of an organic or inorganic liquid is determined by causing it to enter into competition with bathocuproine (BC) in a copper sulphate solution. Bathocuproine (BC) forms stable complexes with the monovalent Cu. Such a reaction is specific for Cu(I) and not for divalent Cu(II). Cu(II) in solution can be reduced to Cu(I) by a number of reducing compositions belonging to a class of compositions consisting prevailingly of both liposoluble and water soluble non-enzymatic antioxidants. When the reaction occurs in a bathocuproine (BC) buffer, the complex being formed is characterized by the concentration of the reducing agents and then, by good approximation, of the antioxidants present in the system. The quantitative analysis of such a reaction can be easily made by spectrophotometry at 480 nm both by macro- and micromethods with the use of a number of reducing standard compositions with known concentrations.

5 Claims, No Drawings

USE OF BATHOCUPROINE FOR THE EVALUATION OF THE ANTIOXIDANT POWER IN LIQUIDS AND SOLUTIONS

CROSS REFERENCE TO RELATED APPLICATION

This application is the 35 USC 371 national stage of International Application PCT/IT99/00289 filed on Sep. 15 1999, which designated the United States of America.

FIELD OF THE INVENTION

The present invention relates to the chemical analysis and more particularly a method of determining the antioxidant power of an organic or inorganic liquid and/or solution by using bathocuproine. According to the invention, the antioxidant power of an organic or inorganic liquid and/or solution is determined by causing it to enter into competition with bathocuproine in a copper sulphate solution. The results compared with the reducing action of uric acid in water solution or α-tocopherol in oil solution with known concentration give values expressed in $\mu$mol/litre.

BACKGROUND OF THE INVENTION

The method used at present for determining the antioxidant power of a sample valid only in water solutions provides the steps of:

providing a solution of ABTS (2,2'-azino-di-3-ethylbenztiazoline sulphonate) with matamioglobine which is a composition stable only 8 hours at room temperature or 48 hours at +2/+8° C.; and causing such solution to enter into competition with the sample to be analyzed in a hydrogen peroxide solution.

SUMMARY OF THE INVENTION

The invention seeks to provide a method of determining the antioxidant power of a liquid and/or solution by using a marker consisting of a stable substance and by providing values expressed in $\mu$mol/litre. It is known that bathocuproine (BC) forms stable complexes with monovalent Cu. Such a reaction is specific for monovalent Cu(I) and not for divalent CU(II). CU(II) in solution may be reduced to Cu(I) by a number of reducing compositions belonging to a class of compositions consisting prevailingly of both liposoluble (tocopherols, carotenoids, etc.) and water soluble (ascorbic acid, uric acid, bilirubin, etc.) non-enzymatic antioxidants.

For instance, Cu (I) formation was monitored using the bathocuproine as specific CU(I) chelator in BIOCHEMICAL JOURNAL, Vol. 322, n.2 pages 425–433, 1997 R. P. Patel :reduction of Cu(II) by lipid hydroperoxide: implications for the copper-dependent oxidation of low-density lipoprotein".

The experiments reported in the overmentioned document exclusively demonstrate that PC liposomes enriched in lipid hydroperoxides (they are not antioxidants) are able to reduce Cu++ to Cu+. This is due to reducing activity of lipid hydroperoxides, but it has nothing to do with any antioxidant activity.

According to the present invention, it is shown that, when the reaction occurs in a bathocuproine (BC) buffer, the complex being formed is characterized by the concentration of the reducing agents and then, by good approximation, of the antioxidants present in the system. The quantitative analysis of such a reaction can be easily made by spectrophotometry at 480 nm both by macro- and micromethods with the use of a number of reducing standard compositions with known concentrations.

One feature of the present invention is the determination of the antioxidant power of the sample (plasma, serum, other biological, non-biological liquids) by adding copper sulphate and measuring Cu(I) ion formed from the reduction of CU (II) ion by all of the present antioxidant substances.

A second peculiar feature of the invention is the detection of Cu(I) ion made by measuring the quantity of Cu(I)-bathocuproine (BC) complex, the latter chelating agent being pure in oil solutions and showing the disulphonate form in water solutions. Such (stable) complex has a typical spectrum of absorption with a maximum at 480–490 nm. The values obtained are quantified by comparison with a standard curve provided by samples having a known concentration of uric acid used as typical reducing agent in water solutions, and α-tocopherol in oil solutions.

DETAILED DESCRIPTION OF THE INVENTION

Further features and advantages of the invention will be more readily apparent from the following description of a preferred embodiment of the method. According to the invention, the determination of the antioxidant power of a sample in water solutions provides the following steps:

1. treating the sample by mixing a 485 $\mu$l buffer (saline solution buffered with 10 mM phosphate at pH 7,4) in a test tube containing bathocuproine disulphonate at a final concentration of 360 $\mu$M with 15 $\mu$l sample, and stirring by Vortex. Basic solution and standard solution are then prepared in the same way by using 15 $\mu$l water and 15 $\mu$l uric acid standard solution with known concentration, respectively. If wells with greater or lower depth are used, a sample dilution of 1:40 should be kept;
2. pouring a 200 $\mu$l quantity of each sample into the wells of a multiwell plate or into single wells;
3. carrying out a first spectrophotbmetry of the samples at 490 nm;
4. adding 50 $\mu$l copper sulphate solution to each well and incubated at room temperature for 3 minutes;
5. adding 50 $\mu$l stop solution (EDTA= ethylendiaminotetraacetic acid) to each well;
6. carrying out a second spectrophotometry of the samples at 490 nm;
7. subtracting the values of the first spectrophotometry from the values of the second spectrophotometry;
8. providing a standard curve from the values relative to the standard samples, i.e. the sample with known concentration of uric acid used as typical reducing agent;
9. calculating the values of the unknown samples on the base of the values obtained from the above standard curve and multiplying them by correction factor 2189 so that the values are expressed as reducing equivalents in $\mu$mol/litre.

According to the invention, the determination of the antioxidant power of a sample in oil solutions provides the following steps:

1. providing an alcohol solution of bathocuproine at the final concentration of 18 nM with a mixture of toluene/ethanol (50:50) Such new solution is mixed in 96 wells at the following ratio: 45,5 ml hexane/ethanol (30:70) mixture +3 ml above mixture containing bathocuproine;

2. diluting the sample at 1:40, and then pouring an amount of 200 μl of each sample into the wells of a multiwell plate or into single wells;
3. carrying out a first spectrophotometry of the samples at 490 nm;
4. adding 50 μl copper sulphate solution to each well and incubating it at room temperature for 3 minutes;
5. adding 50 μl stop solution (triethylentetraamine) to each well;
6. carrying out a second spectrophotometry of the samples at 490 nm;
7. subtracting the values of the first spectrophotometry from the values of the second spectrophotometry;
8. providing a standard curve from the values relative to the standard samples, i.e. the sample with known concentration of α-tocopherol used as typical reducing agent;
9. calculating the values of the unknown samples on the base of the values obtained from the above standard curve and multiplying them by correction factor 1983 so that the values are expressed as reducing equivalents in μmol/litre.

It is self-evident from the foregoing that the method described above has the advantage of using as Cu(I) ion marker a stable complex with a typical spectrum of absorption, thus facilitating the work of the analyst. Moreover, it allows the values to be quantified by simple comparison with a standard curve obtained by samples with a known concentration of a typical reducing agent.

What is claimed is:

1. A method for determining the antioxidant power of an organic or inorganic liquid by using bathocuproine, which comprises:

mixing a sample of said liquid with bathocuproine;
   adding a copper sulphate solution to the obtained mixture;
   determining the quantity of Cu(I) ions formed by reduction of Cu(II) ions by all of the present antioxidant substances, by measuring the quantity of complex formed by Cu(I) and bathocuproine (BC), thereby correlating the determined quantity of Cu(I) ions with the antioxidant power of the liquid.

2. The method for determining the antioxidant power of an organic or inorganic liquid according to claim 1, wherein the liquid is plasma, serum, and other biological liquid.

3. The method for determining the antioxidant power of an organic or inorganic liquid according to claim 1, wherein the liquid is a non-biological liquid.

4. The method for determining the antioxidant power of an organic or inorganic liquid according to claim 1, wherein when said liquid is in water solution, the method comprises the following steps:

a) mixing the sample in a test tube with a buffer containing bathocuproine in a 1:40 ratio, and stirring by Vortex;
   b) preparing a blank solution by using water and standard solutions by using uric acid of known concentration in water solutions;
   c) pouring a predetermined quantity of each of the samples, the blank solution and the standard solutions into the wells of a multiwell plate;
   d) carrying out a first spectrophotometric measurement of the samples at 490 nm;
   e) adding a predetermined quantity of copper sulphate solution to each well and incubating it at room temperature for 1–5 minutes;
   f) stopping the reaction;
   g) carrying out a second spectrophotometric measurement of the samples at 490 nm;
   h) subtracting the values of the first spectrophotometric measurement from the values of the second spectrophotometric measurement;
   i) providing a standard curve from the measurements obtained for the standard solutions with known concentrations of uric acid used as typical reducing agent in water solution;
   j) calculating the quantity of the complex formed by Cu(I) and bathocuproine using the standard curve; and
   k) multiplying said quantity by a correction factor of 2189 so that the quantity is expressed as reducing equivalents in μmol/litre which is correlated with the antioxidant power of the liquid.

5. The method for determining the antioxidant power of an organic or inorganic liquid according to claim 1, wherein when said liquid is in oil solution, the method comprises the following steps:

a) providing an alcohol solution of bathocuproine at the final concentration of 18 nM with a mixture of toluene/ethanol (50:50);
   b) mixing said solution containing bathocuproine with a (30:70) toluene/ethanol mixture at a 1:15 ratio in 96 wells;
   c) diluting the sample at 1:40 in said mixture, preparing standard solutions with known concentrations of α-tocopherol and pouring a predetermined quantity of each of the sample and the standard solutions into the wells of a multiwell plate or into single wells;
   d) carrying out a first spectrophotometric measurement of the samples at 490 nm;
   e) adding a predetermined quantity of copper sulphate solution to each well and incubating it at room temperature for 1–5 minutes;
   f) adding a predetermined quantity of a stop solution (triethylentetraamine) to each well;
   g) carrying out a second spectrophotometric measurement of the samples at 490 nm;
   h) subtracting the values of the first spectrophotometric measurement from the values of the second spectrophotometric measurement;
   i) providing a standard curve from the measurements obtained for the standard solutions with known concentration of α-tocopherol used as typical reducing agent;
   j) calculating the quantity of the complex formed by Cu(I) and bathocuproine using the standard curve; and
   k) multiplying said quantity by a correction factor of 1983 so that the quantity is expressed as reducing equivalents in μmol/litre which is correlated with the antioxidant power of the liquid.

* * * * *